United States Patent [19]

Wong

[11] Patent Number: 4,818,598

[45] Date of Patent: Apr. 4, 1989

[54] ABSORBENT STRUCTURES

[75] Inventor: Arthur Wong, Cincinnati, Ohio

[73] Assignee: The Procter & Gamble Company, Cincinnati, Ohio

[21] Appl. No.: 750,104

[22] Filed: Jun. 28, 1985

[51] Int. Cl.$^4$ ................................................. C08D 5/20
[52] U.S. Cl. ..................................... 428/284; 428/326; 428/913; 521/25; 521/28; 524/52; 524/548; 524/556; 604/368
[58] Field of Search ............... 428/283, 323, 327, 331, 428/402, 280, 281, 282, 913, 284, 326; 521/25, 28; 524/52, 548, 556; 604/368

[56] References Cited

U.S. PATENT DOCUMENTS

| | | | |
|---|---|---|---|
| 3,004,895 | 10/1961 | Schwartz | 167/84 |
| 3,658,790 | 4/1972 | Bernardin | 260/219 |
| 3,691,154 | 9/1972 | Bernardin | 260/219 |
| 3,707,148 | 12/1972 | Bryce | 128/284 |
| 3,793,299 | 2/1974 | Zimmerer | 260/2.2 R |
| 3,889,678 | 6/1975 | Chatterjee et al. | 128/284 |
| 4,020,271 | 4/1977 | Chatterjee | 536/88 |
| 4,026,291 | 5/1977 | Nagano et al. | 128/284 |

FOREIGN PATENT DOCUMENTS 57-45057  3/1982  Japan .
748135  4/1956  United Kingdom .

Primary Examiner—James J. Bell
Attorney, Agent, or Firm—Jerry J. Yetter; George W. Allen; R. C. Witte

[57] ABSTRACT

The present invention relates to absorbent structures in which hydrogel has improved ability to absorb salt-containing fluids due to inclusion within the absorbent structures of fibrous anion exchange materials. The absorbent structures of the present invention comprise hydrogel and fibrous anion exchange material (e.g., DEAE cellulose), and, optionally, fibrous cation exchange materials and/or conventional absorbent materials; said absorbent structures having an equilibrium pH of from about 5 to about 11. The present invention further relates to disposable absorbent products (e.g., diapers, incontinent pads, sanitary napkins) which comprise absorbent structures of the present invention.

21 Claims, No Drawings

ABSORBENT STRUCTURES

TECHNICAL FIELD

The present invention relates to absorbent structures comprising a hydrogel material and a fibrous anion exchange material. Due to the presence of the anion exchange fibers, the hydrogel in the structure has increased absorbent capacity for body fluids, especially urine.

This invention also relates to disposable absorbent products comprising these absorbent structures.

BACKGROUND OF THE INVENTION

Highly absorbent hydrogel materials, typically slightly cross-linked hydrophilic polymers, are known and have been suggested for use in absorbent structures. These materials have a high absorbent capacity for deionized water, typically on the order of 100 times their own weight or more. The absorbent capacity of these materials for body fluids like urine or menses is dramatically lower than for deionized water. It is generally believed that the dramatically lower absorbent capacity for such fluids is caused by the electrolyte content of these fluids and the phenonenon is therefore referred to as the "salt poisoning" effect. It is desirable to increase the absorbent capacity of hydrogels for body fluids so that these materials can be put to a more economical and efficient use.

It is therefore an object of this invention to provide absorbent structures comprising a hydrogel having an increased absorbent capacity for electrolyte-containing fluids. It is a further object of this invention to provide disposable absorbent products, like disposable diapers and sanitary napkins, comprising the absorbent structures of the present invention.

U.S. Pat. No. 4,026,291, issued May 31, 1977 to Nagano et al., discloses the use of diethyl amino cellulose in the absorbent core of an article for treating secreted human fluids. The purpose of the ion exchange fibers in the core is to deodorize, sterilize and coagulate the secreted fluids.

Japanese Patent Application OPI No. 118,846, published Oct. 19, 1976, discloses a combination of anion exchange fibers and cation exchange fibers, such as cellulose and vinyl fibers, whose function is to purify sugar syrups.

Japanese Patent Application OPI No. 45,057, published Mar. 13, 1982, relates to ion exchange resins in powder or granular form which are mixed with hydrogel materials, such as self-crosslinked polyacrylate. The ion exchange materials can be anion exchangers or cation exchangers or a mixture of both. The absorbent capacity of the material is said to be less affected by the presence of salts than conventional absorbent materials.

SUMMARY OF THE INVENTION

The present invention relates to absorbent structures comprising, by weight: (a) from about 1% to about 99% hydrogel; (b) from about 1% to about 99% of a fibrous anion exchange material; (c) from about 0% to about 99% of a fibrous cation exchange material; and (d) from about 0% to about 99% of a conventional absorbent material; said absorbent structure having an equilibrium pH of from about 5 to about 11.

The present invention further relates to disposable absorbent products, such as diapers or sanitary napkins, comprising: (a) a hydrophobic top sheet; (b) a liquid impervious backing sheet; and (c) an absorbent core comprising an absorbent structure of the present invention, said core being placed between the backing sheet and the top sheet.

DETAILED DESCRIPTION OF THE INVENTION

By "hydrogel" as used herein is meant an inorganic or organic compound capable of absorbing aqueous fluids and retaining them under moderate pressures. For good results, the hydrogels must be water-insoluble. Examples are inorganic materials, such as silica gels, and organic compounds, such as crosslinked polymers. Crosslinking may be by covalent, ionic, vander Waals, or hydrogen bonding. Examples of polymers include polyacrylamides, polyvinyl alcohols, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarson et al., Aug. 26, 1975, the disclosures of which are incorporated herein by reference. Particularly preferred polymers for use herein are hydrolyzed acrylonitrile grafted starch, starch polyacrylates, cross-linked polyacrylates, and isobutylene maleic anhydride copolymers, or mixtures thereof. Most preferred are starch polyacrylates and cross-linked polyacrylates.

The hydrogel may have from about 0% to about 100% of its acidic functions groups neutralized with a salt-forming cation. Preferred are hydrogels in which at least about 50%, and more preferably at least about 70%, of the hydrogel acidic functional groups have been neutralized with a salt-forming cation. Preferred salt-forming cations include alkali metal (e.g., potassium; sodium), ammonium, substituted ammonium (such as mono-, di-, tri-, or tetra-alkyl substituted ammonium, with the alkyl groups having from 1 to about 6 carbon atoms; e.g., triethyl or trimethyl ammonium; tetramethyl or tetraethyl ammonium), and amines.

Hydrogel material is used in the form of discrete particles in the absorbent structures of the present invention. Such particles can be of any desired shape, e.g., spherical or semi-spherical, cubic, rod-like, polyhedral, etc. Shapes having a large greatest dimension/smallest dimension ratio, like needles, flakes and fibers, are also contemplated for use herein. Conglomerates of hydrogel particles may also be used.

Although the absorbent structures of the present invention are expected to perform well with hydrogel particles having a particle size varying over a wide range, other considerations may preclude the use of very small or very large particles. For reasons of industrial hygiene, (weight) average particle sizes smaller than about 30 microns are less desirable. Particles having a smallest dimension larger than about 3 mm may also cause a feeling of grittiness in the absorbent structure, which is undesirable from a consumer aesthetics standpoint. Preferred for use herein are particles having an (weight) average particle size of from about 50 microns to about 1 mm. "Particle Size" as used herein means the weight average of the smallest dimension of the individual particles.

Processes for preparing hydrogels are disclosed in U.S. Pat. No. 4,076,663, issued Feb. 28, 1978 to Masuda et al.; in U.S. Pat. No. 4,286,082, issued Aug. 25, 1981 to Tsubakimoto et al.; and further in U.S. Pat. Nos. 3,734,876; 3,661,815; 3,670,731; 3,664,343; 3,783,871; and Belgian Pat. No. 785,858; the disclosures of all of which are incorporated herein by reference.

By "fiber" and "fibrous" as used herein is meant a particle which has a smallest dimension of less than about 100 microns, a second smallest dimension of the same order of magnitude as the smallest dimension, and a longest dimension of at least about 0.5 mm.

By "cation exchange material" is meant a water-insoluble material which is capable of forming releasable ionic bonds with a variety of cations, which has not been fully pH neutralized, and which is not a hydrogel. The material itself is of an anionic nature. It is preferred that the cation exchange material be less than about 50% neutralized, most preferred being the highly protonated form of this material. The cation exchange material has an exchange capacity of more than about 0.1 meq per gram of cation exchange material, with preferred being more than about 0.25 meq/g, and more than about 0.5 meq/g is most preferred.

By "anion exchange material" as used herein is meant a water-insoluble material which is capable of forming ionic bonds with a variety of anions and which has not been fully pH neutralized. The material itself is of a cationic nature. It is preferred that the anion exchange material be less than about 50% neutralized, most preferred being the highly hydroxylated form of this material. The anion exchange material has an exchange capacity of more than about 0.1 meq per gram of anion exchange material, with preferred being more than about 0.25 meq/g, and more than about 0.5 meq/g is most preferred.

Ion exchange fibers for use in the absorbent structures of the present invention can be obtained by introducing cationic groups or anionic groups into natural fibers, for example, cellulose fibers. Good results have been obtained with modification of southern softwood kraft fibers, but northern hardwoods, chemothermal mechanical pulp (e.g., sulfonated chemothermal mechanical pulp ("sulfonated CTMP")), etc. can also be used. Cation cellulosic exchangers can be synthesized by the addition of strong acid groups of the type sulfonate, sulfoethyl, phosphonomethyl, phosphate, carboxylate, and the like. Anionic cellulosic exchangers can be synthesized by the addition of basic groups of the type diethyl amino ethyl, amino ethyl, triethyl amino ethyl, guanidoethyl, paraaminobenzyl, and the like. Methods of making fibrous ion exchange materials are well known in the art, cellulosic ion exchangers being fully described by Peterson in "Cellulosic Ion Exchangers", in *Laboratory Techniques in Biochemistry and Molecular Biology* (Elsevier/North-Holland Biomedical Press; Amsterdam, N.Y., Oxford (1970)), Vol. 2, Part II, pp. 228-396 (1980), the disclosures of which are incorporated herein by reference.

Preferred anion exchange materials comprise modified cellulose materials in fiber form. This includes, for example, diethyl amino ethyl ("DEAE") cellulose, polyethyleneimine ("PEI") cellulose, amino ethyl cellulose, triethyl amino ethyl cellulose, guanidoethyl cellulose, paraaminobenzyl cellulose, ECTEOLA cellulose (triethanolamine coupled to cellulose through glyceryl and polyglyceryl chains), benzoylated DEAE cellulose, and benzoylatednaphthoylated DEAE cellulose prepared by conventional techniques. DEAE cellulose, for example, can be prepared by treating cellulose with a solution of 2-(diethylamino) ethyl chloride. Examples of methods for preparing DEAE cellulose are described in Rousseau et al., *Ind. Eng. Chem. Prod. Res. Dev.*, Vol. 23, pp 250-252 (1984), and in Peterson and Sober,*Biochemical Preparations*, (John Wiley & Sons, Inc., N.Y.-London), Vol. 8, pp. 39-42 (1961), the disclosures of both of which being incorporated herein by reference. Methods for making other anion exchange fibers from cellulose are disclosed in Peterson, "Cellulosic Ion Exchangers", incorporated by reference hereinabove, as well as in Randerath, *Angew. Chem.*, Vol. 74, p. 780 (1962), the disclosure of which is incorporated herein by reference.

Preferred cation exchange materials comprise modified cellulose materials in fiber form. This includes, for example, oxidized cellulose, sulfoethyl cellulose, sulfonated cellulose, phosphonomethyl cellulose, and phosphorylated cellulose ("cellulose phosphate") prepared by conventional techniques. Phosphorylated cellulose, for example, can be prepared by treating cellulose with solutions of urea and phosphoric acid, with phosphorus oxychloride and pyridine, with phosphorus oxychloride and phosphoric acid, with phosphorus oxychloride and dioxane, or with phosphorus oxychloride alone. Examples of methods for preparing phosphorylated cellulose ion-exchanging fibers are described in Bernardin, U.S. Pat. No. 3,691,154, issued Sept. 12, 1972, and Bernardin, U.S. Pat. No. 3,658,790, issued Apr. 25, 1972, both of which are incorporated herein by reference. Methods for preparing other types of ion-exchanging cellulose derivatives are described in Sano et al., U.S. Pat. No. 4,200,735, issued Apr. 29, 1980; Ward et al., U.S. Pat. No. 3,854,868, issued Dec. 17, 1974; and Bridgeford, U.S. Pat. No. 3,533,725, issued Oct. 13, 1970; Zimmerer, U.S. Pat. No. 3,793,299, issued Feb. 19, 1974; and Cuculo, U.S. Pat. No. 3,671,184, issued June 20, 1972; all incorporated herein by reference.

Fibrous cation exchange materials which are derived from pectin-containing vegetable materials may also be used in the present invention. Examples of such materials are citrus absorbent materials ("CAM") and sugar beet-derived materials (e.g., succinylated sugar beet material and phosphorylated sugar beet pulp, preferably in the acid form). These materials are disclosed in European Patent Application No. 84305279.6 by Rich, Publication No. 137611, published Apr. 17, 1985 (synthesis of CAM); European Patent Application No. 84305198.8 by Rich, Publication No. 137608, published Apr. 17, 1985 (absorbent structures containing CAM); and in concurrently-filed U.S. Patent Application for "Absorbent Vegetable Materials" by Goldman et al., Ser. No. 750,567 (synthesis of, e.g., succinylated or phosphorylated sugar beet pulp), the disclosures of all of which are incorporated herein by reference.

Preferred fibrous anion exchange materials for use in the present invention are DEAE cellulose, PEI cellulose, amino ethyl cellulose, triethylaminoethyl cellulose, guanidoethyl cellulose, paraaminobenzyl cellulose, ECTEOLA cellulose, benzoylated DEAE cellulose, and benzoylated-naphthoylated DEAE cellulose; with DEAE cellulose and PEI cellulose more preferred, and DEAE cellulose most preferred. Preferred fibrous cation exchange materials for use in the present invention are cellulose phosphate, sulfoethyl cellulose, sulfonated CTMP, succinylated sugar beet pulp, phosphorylated sugar beet pulp, and CAM, with cellulose phosphate and sulfonated CTMP most preferred.

A typical hydrogel material is a hydrophilic polymer which has been slightly crosslinked. The hydrophilic character of these polymers is due to the presence of hydrophilic groups, typically carboxylic groups. Because of the ionic nature of the hydrophilic groups, they are capable of interacting with ions which may be present in the fluid to be absorbed. A typical example of such electrolytes is sodium chloride in urine. Due to the interaction with the hydrophilic groups on the polymers, the electrolyte in the fluid to be absorbed causes a decrease in the absorbent capacity of the hydrogel. This is referred to as the "salt poisoning effect."

Japanese Patent Application OPI No. 45057, published Mar. 13, 1982, discloses the use of strongly basic anion exchange resins or strongly acidic cation exchange resins or mixtures thereof (in particulate or granular form) in conjunction with a hydrogel. The reference discloses that these combinations provide improved absorbency for a 0.9% NaCl solution. However, the test used allows the absorbent structures to soak in the solution for one hour. Soaking conditions and equilibration times of one hour are, of course, not realistic conditions for absorbent structures which are normally used in disposable absorbent products, e.g., diapers or sanitary napkins. It has in fact been discovered that the particulate or granular ion exchange resins used in that reference do not provide much, if any, benefit when tested in the more realistic absorbency test described hereinbelow.

By contrast, fibrous anion exchange materials have been discovered in the present invention to improve the absorbency performance of hydrogels for salt-containing fluids, under test conditions which closely simulate real use conditions. In addition, it has been discovered that fibrous cation exchange materials do not improve, or even slightly decrease, the absorbency performance of hydrogels for salt-containing fluids, under the same test conditions. However, an additional surprising discovery of the present invention is that (within limits fully given below) when both fibrous cation exchange materials and fibrous anion exchange materials are included in the hydrogel-containing absorbent structure, the absorbency performance of the hydrogel is improved even more than the improvement observed by adding only fibrous anion exchange materials to the hydrogel-containing structure. Finally, it has now been discovered that the improved performance by the hydrogels in the absorbent structures which contain fibrous anion (or anion/cation) exchange materials is not lost after a period of time when subjected to additional fluid loading. This last discovery is particularly important for the design of diapers or sanitary napkins where there is additional fluid added to the absorbent structure after an initial wetting.

Use of the absorbent structures of the present invention in disposable absorbent products, especially diapers and incontinent pads, has several advantages over the art. First, because the absorbent structures of the present invention have increased hydrogel capacity (relative to conventional absorbent structures containing the same weight percent of hydrogel), the disposable absorbent products of the present invention are able to hold more salt-containing fluids. Therefore, replacement of conventional absorbent structures on a equal weight-by-weight basis with absorbent structures of the present invention results in a gain in absorbent capacity. Also, the replacement by the absorbent structures of the present invention may be on a less than equal weight basis, giving a lighter disposable absorbent product having an absorbent capacity equal to the heavier conventional disposable absorbent product.

Another advantage of the present invention is that the weight percent of the relatively expensive hydrogel component in the absorbent structures of the present invention may be reduced relative to conventional absorbent structures without any loss in absorbent capacity. This permits a reduction in cost for making disposable absorbent products of the present invention.

Finally, the absorbent structures of the present invention are observed to have an advantage over the art due to significantly fewer incidents of leakage when less than fully saturated. Thus, the disposable absorbent products of the present invention are expected to have a reduced incidence of low load failure.

While not intending to be limited by theory, it is believed that the observed difference in hydrogel performance between fibrous and resinous ion exchange-containing hydrogel absorbent structures is the result of hydration kinetics and/or ion exchanger kinetics. It is believed that the performance of the hydrogel is not improved by the ion exchange material until the ion exchange material becomes fully hydrated, and that the fibrous ion exchange material hydrates faster than the ion exchange resins. Thus, under typical usage conditions (which require rapid absorption of high volumes of salt-containing fluids, and rapid ion exchange (i.e., salt removal) of salt containing fluids), the more quickly hydrated fibrous material results in the observed improved hydrogel performance relative to resins. In addition, it is believed that the fibrous material is better able to physically interact with the hydrogel (i.e., more intimate contact by fibrous material with hydrogel) than resins, thereby making the cation/anion and acid/base interactions between the hydrogel and the fibrous material more facile.

It is to be noted that besides improving hydrogel performance, the fibrous ion exchange materials, themselves, provide benefits to absorbent structures that ion exchange resins do not. The fibrous ion exchange materials give structural strength to the absorbent structures. In addition, the fibrous ion exchange materials are much better able to absorb fluids than ion exchange resins and thus these fibers add additional absorbency to absorbent structures.

The absorbent structures of the present invention take advantage of acid-base interactions between the hydrogel and fibrous anion exchange material, or hydrogel and fibrous anion/cation exchange materials, to reduce the salt poisoning effect (via ion exchange of salt-containing fluids) on the hydrogel. It has now been observed that hydrogel performance varies according to the equilibrium pH of the absorbent structure. The "equilibrium pH" of the absorbent structure is the average surface pH of the absorbent structure when fully saturated with "synthetic urine" (fully described in the Performance Testing section hereinbelow). This average surface pH is the average of 5 surface pH measurements taken with a surface pH probe (Markson Science, Phoenix, Ariz., Model No. H-1208), the 5 measurements being done on the circular test sample used in the Performance Testing (described hereinbelow) at the positions on the circle of 12, 3, 6, and 9 o'clock, and at the center of the circle. The equilibrium pH of the absorbent structure is a function of the relative proportions of fibrous cation exchange material, fibrous anion exchange material, and hydrogel contained within the structure.

It is possible to achieve a certain equilibrium pH in the hydrogel-containing absorbent structure by choosing an appropriate cation fiber/anion fiber ratio (meq/g: meq/g). For example, ratios on the order of 2:1 or even 1:1 will maintain a relatively low pH. The choice of the preferred cation/anion exchange ratio will ultimately depend on the intended use of the absorbent structure. If, based on the intended use, the absorbent capacity is to be optimized, one would use a low cation/anion exchange ratio (such as below about 1:1, preferably from about 1:1 to about 1:10), or even anion exchange fibers as the sole exchange material. If, on the other hand, pH control is important (for example, to prevent odor development in menstrual fluids), the preferred ratio is from about 1:1 to about 10:1, more preferably being from about 1:1 to about 3:1, with from about 1:1 to about 2:1 most preferred.

It has been observed that optimum improvement in hydrogel performance occurs at an equilibrium pH of from about 6.5 to about 9. As the contents of the absorbent structure is varied so as to vary its equilibrium pH (e.g., by adding more fibrous anion exchange material to make the absorbent structure more basic, or adding more fibrous cation exchange material or hydrogel to make the absorbent structure more acidic), the improvement in hydrogel performance falls off slightly as the equilibrium pH increases above about 9, but it is observed that performance falls off dramatically below an equilibrium pH of about 5.3 to the point that little or no improvement is observed below about equilibrium pH=5.0. Thus, in light of the observed correlation between improved hydrogel performance and absorbent structure equilibrium pH, and because the equilibrium pH of the absorbent structure is a function of the composition of the absorbent structure, the absorbent structures of the present invention may be defined in terms of their equilibrium pH.

It is to be noted that in addition to the fibrous ion exchange materials and the hydrogel material, the absorbent structures of the present invention can further contain other materials as are typically employed in absorbent structures, hereinafter referred to as "conventional absorbent materials". Examples of conventional absorbent fibers include vegetable fibers like cotton fibers, wood pulp fibers (e.g., Kraft pulp fibers, chemo-thermo mechanical pulp fibers), and fibers of abaca, sisal, heneguen, cantala, istle, mauritirus, phornium, sansevieria, caroa, plassava, broomroot, flax, hemp, ramie, jute, kenaf, roselle, urena, coir and kapok. Typical examples of conventional absorbent materials further include manmade fibers like rayon, cellulose acetate, cellulose triacetate, protein fibers, polyamide, nylon-6,6, nylon-6, aromatic polyamides, polyester, acrylic fibers, polyethylene and polypropylene fibers. Many of the manmade fibers are hydrophobic, but can be hydrophilized using art-disclosed techniques. Hydrophobic fibers may be hydrophilized by surfactant treatment as disclosed in U.S. Pat. No. 3,916,447, issued Nov. 4, 1975 to Thompson, and in U.S. Pat. No. 4,100,324, issued July 11, 1978 to Anderson et al., the disclosures of which are incorporated herein by reference. Thermoplastic fibers may further be hydrophilized by coating with a hydrophilic material, e.g. silica, or by surface grafting to fibers with hydrophilic groups. Absorbent materials comprising silica film coatings are disclosed in U.S. Pat. No. 4,469,746, issued Sept. 4, 1984, to Weisman et al., incorporated herein by reference.

Therefore, the present invention relates to absorbent structures comprising (by weight): (1) from about 1% to about 99% hydrogel, preferred being from about 1% to about 50%, with from about 1% to about 10% most preferred; (2) from about 1% to about 99% of a fibrous anion exchange material, preferred being from about 1% to about 70%, with from about 1% to about 60% most preferred; (3) from about 0% to about 99% of a fibrous cation exchange material, with from about 0% to about 50% preferred; and (4) from about 0% to about 99% of a conventional absorbent material, with from about 0% to about 50% preferred; with said absorbent structure having an equilibrium pH of from about 5 to about 11, with a pH of from about 5.3 to about 9 preferred, and a pH of from about 5.3 to about 7.0 most preferred. It is further preferred that the absorbent structures contain a fibrous cation exchange material; and it is preferred that these structures have a fibrous cation: anion material ratio (meq/g:meq/g) in the range of from about 10:1 to about 1:10, with a range of from about 3:1 to about 1:10 preferred, and from about 2:1 to about 1:3 most preferred.

It is to be noted that the higher the exchange capacity (meq/g) of the fibrous anion or cation exchange material used to prepare the absorbent structure, the lower the weight percent of the exchange material needed in the absorbent structure to be effective in improving hydrogel performance. It is preferred that the fibrous cation and anion exchange materials used in the absorbent structures of the present invention have an exchange capacity of at least about 0.25 meq/g, and preferably at least about 0.5 meq/g.

The improved absorbency performance by the hydrogel in absorbent structures of the present invention allows the use of a smaller weight percent of the hydrogel to get an equal amount of fluid to be absorbed by the absorbent structure. Thus, from a cost-benefit viewpoint, the present invention provides a greater cost savings (by requiring the use of smaller amounts of the relatively expensive hydrogel to get the same absorbency) when higher weight percents of hydrogel would otherwise have been used in conventional absorbent structures. However, it is generally not necessary, or economically or structurally desirable, to use more than about 50% of hydrogel in an absorbent structure. Thus, it is preferred for most disposable absorbent products that the absorbent structures of the present invention comprise from about 1% to about 50% hydrogel, with from about 1% to about 10% most preferred. In addition, from a cost-benefit analysis standpoint, it is preferred that the absorbent structures of the present invention comprise from about 1% to about 70% of fibrous anion exchange material (with from about 1% to about 60% most preferred); from about 0% to about 50% of fibrous cation exchange material; and from about 0% to about 50% conventional absorbent material.

When constructing the absorbent structures of the present invention, the structure may consist of layers of the various components, or the structure may be a homogeneous mixture of some or all of the components. Examples of layered structures of the present invention are: 1) layers of mixed cation/anion exchange fibers alternating with hydrogel/cellulose fiber layers; 2) a layer of cation exchange fiber positioned over a layer of anion exchange fiber over a layer of hydrogel/cellulose fiber; and 3) a layer of anion exchange material and a layer of hydrogel sandwiched between layers of cellulose fiber. It is preferred that the absorbent structures be a homogenous mixture of all the components of the absorbent structure.

The absorbent structures of the present invention may conveniently be made by using conventional equipment designed for air laying of hydrophilic fibrous webs. In such equipment, webs are typically formed by taking up hydrophilic fibers in an air flow and depositing the fibers on a wire mesh screen. By metering the desired quantities of absorbent material particles or fiber particles into the air flow at a point just upstream of the wire mesh screen, the desired mixture of ion exchange fibers, hydrogel and other absorbent material can be made. The web formed on the screen is then passed through calender rolls which are set to a nip pressure resulting in the desired density of the absorbent structure. It will be clear that this embodiment of the process requires only minor modifications of conventional equipment for the manufacture of absorbent structures, i.e. installing a metering device for the addition of the absorbent materials. In certain instances it may be necessary to replace the standard wire mesh screen on the equipment with one of a finer mesh size. This need will arise if relatively small particles are used, and/or when the mesh size of the standard screen is relatively coarse.

Optionally, the structures may be compressed to a higher density than that of conventional air-laid wood pulp fiber webs (i.e., a density higher than about 0.1 g/cm$^3$) by increasing the nip pressure on the calender rolls. The densified absorbent structures generally have good absorbent properties, in spite of their reduced void volume, and better wet strength and dry strength than non-densified structures. This is due to the wet resiliency exhibited by the material. It regains virtually all of its original volume if wetted in a densified state and therefore exhibits its high absorbency in both an uncompressed and compressed state (unlike wood pulp fiber webs which become distinctly less absorbent upon compression). The densified structures therefore have properties (low bulk, high absorbency) which are highly desirable for absorbent products like disposable diapers, incontinent pads and sanitary napkins. The densified structures have a density of from about 0.1 g/cm$^3$ to about 1 g/cm$^3$, preferably from about 0.15 to about 0.5 g/cm$^3$. Densified absorbent structures are disclosed in European Patent Application No. 84301578.5 by Weisman et al., Publication No. 122042, published Oct. 17, 1984, incorporated herein by reference.

Alternatively, an absorbent structure may be formed by placing a web of absorbent fibers against a sheet of one of the absorbent structures described above. Optionally, the sheet and/or the web may be wrapped in envelope tissue, to increase the lateral strength of the structure. Absorbent structures of the present invention also include laminates comprising one or more sheets of absorbent material and one or more sheets of one of the absorbent structures described above, e.g. a laminate of one sheet of water-insoluble hydrogel placed against a sheet comprising hydrogel and fibrous anion exchange material; or a "sandwich" type laminate, comprising a sheet of water-insoluble hydrogel material placed in between two sheets comprising hydrogel and fibrous anion exchange material. Many variations are possible, as will be apparent to those skilled in the art.

Alternatively, an absorbent structure can be formed by mixing absorbent fibers, e.g., wood pulp fibers, hydrogel, and fibrous ion exchange material in an aqueous slurry; admixing a surfactant; and foaming with air. The foamed slurry is then conveyed onto a wire screen and dewatered, preferably by applying vacuum to the underside of the wire screen. The foamed mat thus obtained is subsequently dried in air. A more detailed description of the foaming process is disclosed in U.S. Pat. No. 3,871,952, issued Mar. 18, 1975 to Robertson, incorporated herein by reference. As above, the mixture can be densified to a density of about 1 g/cm$^3$ without significant loss of absorption capacity, more preferred being structures having a density of from about 0.15 to about 0.5 g/cm$^3$.

In addition, the absorbent structures of the present invention can contain other components appropriate for the specific properties desired of the structure (e.g., wet strength additives, binders, etc.). For example, to improve the strength of the absorbent structures of the present invention the structures can be mixed with a small amount (typically from about 0.5% to about 5%) of a long thermoplastic fiber. As used herein, long fiber means a fiber having a length of more than about 1 inch (about 2.5 cm). Suitable thermoplastic materials are inexpensive polymers like polyethylene, polypropylene and polyester. Polyester fibers are preferred because they are more hydrophilic than polyolefin fibers. The use of thermoplastic fibers in absorbent structures for the purpose of improving the strength of such structures is described in more detail in U.S. Pat. No. 4,307,721, issued Dec. 29, 1981 to Tsuchiya et al.,; U.S. Pat. No. 4,219,024, issued Aug. 26, 1980 to Patience et al.; and in U.S. Pat. No. 4,100,329, issued July 11, 1978 to Anderson et al.; the disclosures of all of which are incorporated herein by reference. Other additives will be apparent to those skilled in the art.

Because of their particular properties, the absorbent structures of this invention are very well suited for use in disposable absorbent products. By "disposable absorbent product" herein is meant a consumer product which is capable of absorbing significant quantities of water and other fluids, particularly body fluids (e.g., urine; menses), and especially urine. Examples of disposable absorbent products include disposable diapers, sanitary napkins, incontinent pads, paper towels, facial tissues, bandages and the like. The absorbent structures of the present invention are particularly suitable for use in products like diapers, bandages, incontinent pads, and sanitary napkins. Through their use, it is possible to design absorbent products which are thin and yet have more than sufficient absorbent capacity to avoid the embarrassment and inconvenience of failure. Flexibility of the structure ensures comfort for the wearer and a good fit of the absorbent product.

Disposable diapers comprising the absorbent structures of the present invention may be made by using conventional diaper making techniques, but replacing the wood pulp fiber web core which is typically used in conventional diapers with an absorbent structure of the present invention. Disposable diapers are fully described in Duncan and Baker, U.S. Pat. No. Re 26,151, issued Jan. 31, 1967; Duncan, U.S. Pat. No. 3,592,194, issued July 13, 1971; Duncan and Gellert, U.S. Pat. No. 3,489,148, issued Jan. 13, 1970; Buell, U.S. Pat. No. 3,860,003, issued Jan. 14, 1975; and Duncan, U.S. Pat. No. 3,952,745, issued Apr. 27, 1976; which patents are all incorporated herein by reference. A preferred disposable diaper for the purpose of this invention comprises an absorbent core containing an absorbent structure of the present invention; a topsheet superposed or co-extensive with one face of the core; and a liquid impervious backsheet superposed or co-extensive with the face of the core opposite the face covered by the topsheet. The diaper may further comprise a second absorbent core, like a wood pulp fiber web, or a sheet of water-insoluble hydrogel. The backsheet most preferably has a width greater than that of the core thereby providing side marginal portions of the backsheet which extend beyond the core. The diaper is preferably constructed in an hourglass configuration. Incontinent pads are similarly constructed, but typically contain higher weight percents of hydrogel.

The backing sheet (or backsheets) of the disposable absorbent products herein can be constructed, for example, from a thin, plastic film of polyethylene, polypropylene or other flexible moisture impeding material which is substantially water impervious. Polyethylene, having an embossed caliper of approximately 1.5 mils, is especially preferred.

The topsheet of the disposable absorbent products herein can be made in part or completely of synthetic fibers, such as polyester, polyolefin, rayon, or the like, or of natural fibers, such as cotton. The fibers are typically bound together by a thermal binding procedure or by a polymeric binder such as polyacrylate. This sheet is substantially porous and permits a fluid to readily pass therethrough into the underlying absorbent core. The topsheet can be made more or less hydrophobic depending upon the choice and treatment of fiber and binder used in the construction thereof. The topsheets used in the articles of the present invention are relatively hydrophobic in comparison with the absorbent core of said articles. Topsheet construction is generally disclosed in Davidson, U.S. Pat. No. 2,905,176, issued Sept. 22, 1959; Del Guercio, U.S. Pat. No. 3,063,452, issued Nov. 13, 1962; and Holliday, U.S. Pat. No. 3,113,570, issued Dec. 10, 1963; which patents are incorporated herein by reference. Preferred topsheets are constructed from polyester, rayon, rayon/polyester blends or polypropylene.

Because the absorbent structures of the present invention are highly absorbent, and yet thin and flexible, they are well suited for use in sanitary napkins. As is the case with disposable diapers, sanitary napkins utilizing the present absorbent structures may be derived from conventional sanitary napkins by simply replacing the absorbent core thereof (typically a web of wood pulp fibers) with an absorbent structure of the present invention. Such replacement may be on a weight-by-weight basis, which results in a reduction in volume and a gain in capacity; or the replacement may be on a less than equal weight basis; thereby sacrificing part of the gain in absorbent capacity in favor of an even greater reduction in bulk. Further reduction in bulk is possible by utilizing densified absorbent structures of the present invention.

An example of a sanitary napkin comprises a pad of the absorbent structure of the present invention; a hydrophobic topsheet; and a fluid impervious bottom sheet. The topsheet and the backsheet are placed at opposite sides of the absorbent structure. Optionally, the absorbent structure is wrapped in envelope tissue. Suitable materials for top sheets, bottom sheet and envelope tissue are described more fully above and are well known in the art. A more detailed description of sanitary napkins and suitable materials for use therein is found in U.S. Pat. No. 3,871,378, issued Mar. 18, 1975 to Duncan et al., the disclosures of which are incorporated herein by reference.

Performance Testing A. Partition Test Procedures

Samples of absorbent structures of the present invention are subjected to a partitioning test, more fully described hereinbelow. This test is designed to measure the absorption performance of hydrogel when used in an absorbent structure, both under conditions of low liquid load and high liquid loads. The absorption fluid utilized is "synthetic urine" (a solution of 1% NaCl, 0.06% $MgCl_2.H_2O$ and 0.03% $CaCl_2.H_2O$ in distilled water, the surface tension of the solution being adjusted to 45 dynes/cm with about 0.0025% of an octylphenoxy polyethoxy ethanol surfactant (Triton X-100, from Rohm and Haas Co.)). This test is predictive of the absorption capacity under typical usage conditions of absorbent materials when used as absorbent cores in diapers.

The partitioning tests are carried out as follows. A piece of vinyl acetate sheet is placed on a flat, nonabsorbent surface. A round sample (57 mm diameter) of the absorbent structure to be tested is placed on top of this vinyl acetate sheet. A piece of tissue paper (57 mm diameter) of the type generally used as envelope tissue in disposable diapers is placed on top of the test sample. On top of the envelope tissue is placed a sample of the reference material (southern softwood fibrous web, 0.1 $gm/cm^3$; Foley fluff obtained from Buckeye Cellulose Co., Memphis, Tenn.). Both test sample and reference sample are prepared to have a similar sample weights, i.e. basis weight. The top sample is wetted with a predetermined amount (about a 2X loading) of synthetic urine and then covered with a piece of polyethylene sheet (76 mm diameter). This polyethylene sheet is similar to the kind of material generally used as a backsheet in disposable diapers. A confining weight of 4.4 pounds (about 2 kg) is placed on top of the polyethylene sheet. This weight exerts a confining pressure of 1 psi (about $7 \times 10^3 N/m^2$) (when confined the samples have a diameter of about 60 mm). After five minutes equilibration time, the weight is removed and the two samples of absorbent material are weighed separately. The "X-load", defined as the amount of synthetic urine (in grams) absorbed per gram of absorbent material is calculated for each of the samples. The sample is then placed under the confining weight, and dosed with an additional dose of synthetic urine, equilibrated, and weighed. This is repeated several times (typically 8 to 10 times) so that the relative absorption performance of the test material over a wide range of X-loads is obtained as a function of the loading in the reference top layer.

B. Test Sample Preparation Procedures

Individual test samples are prepared by homogeneously mixing various fiber blends together in a Galaxie Osterizer blender utilizing an 8 ounce blender bottle for 15 seconds at the mix speed. The test sample is then removed from the blender bottle and placed in a 63 mm diameter tin lid and compressed to the desired density. By using a small spatula, the sample is removed and punched out with a 57 mm diameter punch. Each sample is checked for correct basis weight and caliper. When the test samples have a basis weight of 0.035 $gm/cm^2$, the total weight of the components that is added into the blender bottle is 1.1 grams. When the test samples had a basis weight of 0.025 $gm/cm^2$, the total weight of the components that is added into the blender bottle is 0.75 grams.

C. Reference Sample Preparation Procedure

Large sheets of reference sample cores are made by air laying 10"×16" (25 cm×40 cm) sheets of defibered southern softwood pulp (Foley fluff obtained from Buckeye Cellulose Co., Memphis, Tennessee). Sheets are air laid corresponding to the required basis weight of the test sample. The sheets are then compressed to 0.1 gm/cm$^3$ density. Before each partition test, samples of the reference material are punched out (57 mm diameter) and density and basis weight are checked and adjusted if necessary.

D. Calculation of Effective Hydrogel Capacity

After partition tests are completed, relative absorption performance of the test material over a wide range of X-loads is obtained as a function of the loading in the reference top layer. These results are compared to other partition test results where sample conditions are the same, i.e., basis weight, density, and equilibrium time. Also, to determine the effectiveness of the ion exchange fiber systems in increasing the ability of the ion exchange fiber/hydrogel systems to hold more ionic solution than the non-ion exchange fiber/hydrogel systems, it is assumed that the total absorption capacity of the test sample is made by the fractional absorption capacity of the individual components in the test sample. From this assumption the "effective hydrogel capacity", which is a measure of the absorbency of hydrogel within an absorbent structure, can be determined by the following equation:

$$C_{ss} = \frac{C_{sys} - [(C_1 \times X_1) + (C_2 \times X_2) + \ldots (C_n \times X_n)]}{X_{ss}}$$

where
- $C_{ss}$ = effective hydrogel capacity (X-load)
- $X_{ss}$ = weight fraction of hydrogel in test sample
- $C_{sys}$ = test sample X-load
- $C_1$ = X-load of component 1 in neat test sample
- $X_1$ = weight fraction of component 1 in test sample
- $C_2$ = X-load of component 2 in neat test sample
- $X_2$ = weight fraction of component 2 in test sample
- $C_n$ = X-load of component n in neat test sample
- $X_n$ = weight fraction of component n in test sample As seen from the above equation, any number of components can be in the test sample. The effective hydrogel capacity can be calculated as long as partition data has been obtained for the pure (neat) components of the test sample. These background supporting data are obtained for the neat components under the same conditions as for the test sample, i.e., similar basis weights, densities, absorption fluid, confining pressure, and equilibrium time. In using the above equation, the individual X-load of the neat components is used at the same reference top layer X-load of the test sample. In general, the larger the value of the effective hydrogel capacity, the better the ion exchange fiber/hydrogel system is in its ability to increase the utilization (or efficiency) of the hydrogel in the test sample to hold fluids. Also, in general, when comparing the partition test results, a higher value of fluid capacity (X-load) in the test layer with respect to a specific X-load in the reference top layer, indicates better performance for a given test sample. Comparisons again should be based on similar test conditions, i.e., similar basis weights, densities, absorption fluid, confining pressure, and equilibrium time.

EXAMPLE I

Absorbent Structures Containing Anion Exchange Fibers (a) Synthesis of DEAE Cellulose 2000 grams of never-dried wet lap Foley fluff (46% solids; southern softwood kraft pulp obtained from Buckeye Cellulose Co., Memphis, Tenn.) is mercerized in 6 liters of cold (0° to 5° C.) 22% NaOH solution for 30 minutes. Complete wetting of the pulp is achieved by constant slow speed stirring of the pulp slurry (11.5% solids) in a commercial Hobart mixer. After the 30 minutes of mercerization, 5.3 kg of a 2-(diethylamino) ethyl chloride hydrochloride solution ("DEAE-Cl.HCl"; made by dissolving 2.3 kg DEAE-Cl.CHl in 3.0 liter distilled water) is added to the pulp-mercerization slurry. The resultant pulp slurry mixture is mixed with the commercial Hobart mixer and heated for 45 minutes with the reactor temperature never exceeding 83° C. After this time additional base (1.06 kg of 51.2% NaOH solution) is added to the pulp slurry. The resulting mixture is stirred for 20 minutes at a reactor temperature of 83° C., followed by turning off the heat source, adding base (1.06 kg of 51.2% NaOH solution), and then continuing stirring for another 2 minutes.

After allowing for some pulp slurry settlement, 4.5 liter of the liquid portion is removed from the reactor kettle. Additional fresh base (6.0 kg of 22.1% NaOH solution) is then added to the stirred and heated reaction mixture. Immediately following the base addition, 3 liter of a 4.5 M DEAE-Cl.HCl solution is added. After mixing for 15 minutes at 83°-88° C., base (1.06 kg of 51.2% NaOH solution) is added to the mixture. After heating at 83°-85° C. with stirring for another 20 minutes, the heating and stirring is stopped, the pulp is allowed to partially settle, and 5.0 liter of reaction solution is removed. The hot pulp slurry is then cooled to 10° C. in an ice bath, and 5.0 liter of 2M NaCl solution is added and mixed into the pulp slurry to deswell the modified pulp fibers.

The pulp slurry solution is removed from the pulp fibers by filtering the modified pulp on a Buchner funnel under vacuum. The modified pulp is washed 2X with water (2% solids) and filtered to remove reactants and by-products. The modified pulp is then washed with a 2M HCl solution (2% solids) and filtered (effluent had pH=2) to remove unreacted DEAE and neutralize excess base, followed by washing 3X with water (2% solids) and filtering. A base wash (2% solids) and filtration is then performed which consists of adding enough 1N NaOH to the slurry to achieve pH=11. This is followed by an acid wash (2% solids) and filtration which consists of adding enough 1 N HCl to the slurry to achieve a pH of 1 to 2.5. After washing 3X with water (2% solids) and filtering, a final base wash and filtration is performed to ensure that the modified pulp is in the base form. This step consists of making a slurry (2% solids) and adding enough 1 N NaOH to achieve pH=11. The modified pulp is then washed and filtered repeatedly with distilled water until the filtrate is pH neutral. The wet DEAE cellulose is then freeze dried at the 6% consistency level. The process yields DEAE cellulose in the OH$^-$ form which has an ion-exchange capacity of about 2.15 meq/g (determined by titration).

(b) Preparation of Absorbent Structures

DEAE cellulose prepared as in part (a) above is mixed, using conventional air laying equipment to form webs, with acrylic acid grafted starch hydrogel which is about 70% neutralized ("Sanwet IM-1000", from Sanyo Chemical Industries, Ltd., Japan) in a weight ratio of 85% to 15%. This web is then compressed using a conventional pressing device to densify the structure to about 0.25 g/cm$^3$. This absorbent structure, which has an equilibrium pH of about 8.5, possesses excellent absorbent properties, especially for urine, and is suitable for use in, e.g., diapers, incontinent pads, and sanitary napkins.

Other absorbent structures of the present invention having an equilibrium pH of from about 5 to about 11 are similarly made using the following components and weight percents:

(1) 95% of DEAE cellulose (exchange capacity=1.5 meq/g) and 5% of Sanwet 1M-1000, densified to 0.15 g/cm$^3$ (equilibrium pH is about 8.5);

(2) 95% of PEI cellulose (exchange capacity=0.2 meq/g) and 5% of 75% neutralized cross-linked polyacrylate, densified to 0.2 g/cm$^3$ (equilibrium pH is about 7.0);

(3) 50% of DEAE cellulose (exchange capacity=2.5 meq/g) and 50% of Sanwet IM-1000, densified to 0.25 g/cm$^3$ (equilibrium pH is about 8);

(4) 65% of DEAE cellulose (exchange capacity=2.0 meq/g), 15% of Sanwet IM-1000, and 20% of Foley fluff, densified to 0.2 g/cm$^3$ (equilibrium pH is about 8.5).

These absorbent structures possess excellent absorbent properties, especially for urine, and are suitable for use in, e.g., diapers, incontinent pads, and sanitary napkins.

EXAMPLE II

Absorbent Structures Containing Anion and Cation Exchange Fibers (a) Synthesis of Cellulose Phosphate 76.5 grams of wet never-dried Foley fluff (40.8% solids; southern softwood kraft pulp obtained from Buckeye Cellulose Co., Memphis, Tenn.) is added to 3500 grams of a urea/85% phosphoric acid/water mixture (36.4%/23.2%/40.4% by weight) in a commercial Waring blender, and the resulting mixture is mixed for 30 seconds at low speed. In a 6 inch×6 inch (about 15 cm×15 cm) Deckel Box, enough of a urea/85% phosphoric acid/water solution (36.4%/23.2%/40.4% by weight) is added to fill the box to the 100 mesh stainless steel wire screen, and then the above well mixed pulp slurry is wet laid in the Deckel Box. After draining of the solution, the wet impregnated pulp mass is removed from the Deckel Box and placed in a forced draft oven at 140° F. (about 60° C.) until the pulp mass is dry.

The pulp mass is then cured in a forced draft oven at 320° F. (about 160° C.) for 1 hour, during which time ammonia is observed to be expelled from oven vents. The cured pulp mass is then placed into 2.3 liters of 150° F. (about 65° C.) distilled water, and heated with stirring to disperse the cured pulp into the water. After the pulp is completely dispersed, it is dewatered on a Buchner funnel, the water effluent being very acidic (pH=1). This hot water washing is repeated (again using 2.3 liters of distilled water) followed by filtration. The pulp is then acid washed for 10 minutes in a stirred solution made up of 30 ml concentrated HCl and 2.3 liters distilled water, after which the pulp is filtered on a Buchner funnel. The pulp is then washed and filtered several times with distilled water until the effluent is pH neutral. The final wet pulp mass is freeze dried at 6% consistency to obtain dry cellulose phosphate.

(b) Preparation of Absorbent Structures

DEAE cellulose (exchange capacity=1.1 meq/g), cellulose phosphate (exchange capacity=2.1 meq/g), and Sanwet IM-1000 are mixed using conventional air laying equipment to form webs in a weight ratio of 75%:10%:15%. This web is then compressed using a conventional pressing device to densify the structure to about 0.25 g/cm$^3$. This absorbent structure (equilibrium pH of about 6.8) possesses excellent absorbent properties, especially for urine, and is suitable for use in, e.g., diapers, incontinent pads, and sanitary napkins.

Other absorbent structures of the present invention having an equilibrium pH from about 5 to about 11 are similarly prepared by (1) using 65% of DEAE cellulose, 20% of cellulose phosphate, and 15% Sanwet IM-1000 (equilibrium pH of about 5.8); (2) using 60% of DEAE cellulose, 25% of cellulose phosphate, and 15% Sanwet IM-1000 (equilibrium pH of about 5.4); (3) substituting crosslinked polyacrylate for the Sanwet IM-1000; and (4) adding 20% Foley fluff to the absorbent structure.

These absorbent structures possess excellent absorbent properties, especially for urine, and are suitable for use in, e.g., diapers, incontinent pads, and sanitary napkins.

EXAMPLE III

Absorbent Structures Containing Additional Components

A polyester-reinforced absorbent structure is prepared as follows:

6 denier polyester fiber, fiber length about 4 in. (about 10 cm), is carded and formed into an unbound web, and then placed on a wire screen which is covered with a tissue. A mixture of DEAE cellulose and Sanwet IM-1000 (85%:15% by weight) is poured over the polyester fiber web, and forced into the web by reducing the air pressure under the wire screen. The resulting structure is compressed in a flat hydraulic press to a density of 0.2 g/cm$^3$. This absorbent structure, which contains polyester fiber: DEAE cellulose:Sanwet IM-1000 in a weight ratio of 5%:80.75%:14.25%, posseses excellent absorbent and strength properties, and is suitable for use in, e.g., diapers, incontinent pads and sanitary napkins.

EXAMPLE IV

Diapers Employing an Absorbent Structure

Disposable diapers utilizing absorbent structures of the present invention are prepared as follows:

The absorbent structure prepared as in Example II is enveloped in wet strength tissue paper having a basis weight of about 12 pounds per 3,000 square feet (about 20 g/m$^2$), a dry tensile strength of about 700 g/inch (about 275 g/cm) in the machine direction and about 300 g/inch (about 120 g/cm) in the cross machine direction.

The enveloped pad is glued onto a 7 in.×11 in. (about 18 cm×28 cm) backsheet of embossed polyethylene film having a melt index of about 3 and a density of about 0.92 g/cm$^3$. The ends of the backsheet are folded over the enveloped pad and attached with glue. Finally, the absorbent pad is covered with a topsheet of hydrophobic but water and urine pervious material. (Webline No. F 6211 from Kendall Co. of Wapole, Mass., comprised of a non-woven rayon bonded with an acrylic latex). The resulting absorbent structure is useful as a diaper and has excellent properties of absorption and containment of urine.

EXAMPLE V

Sanitary Napkins Employing an Absorbant Structure

Sanitary napkins utilizing absorbent structures of the present invention are prepared as follows:

An absorbent structure, prepared as in Example II, is calendered to a density of about 0.4 g/cm$^3$ as measured under a confining pressure of 0.1 PSI (about $7\times10^3$ N/m$^2$). The web is cut into a pad of 8 in.$\times$2 in. (about 20 cm$\times$5 cm) with tapered ends. On top of this pad is placed a second pad (rectangular) of 5 in.$\times$2 in. (about 13 cm$\times$5 cm). The combined pad structure is placed against a waterproof backing sheet (8 in.$\times$2 in. (about 20 cm$\times$5 cm) tapered) of embossed hard polyethylene having an embossed caliper of 1.5 mils. The structure is covered with a top sheet of non-woven, 3 denier needle punched polyester fabric having a density of about 0.03 g/cm$^3$ and a caliper of about 2.3 mm. The thus covered structure is placed on a 9 in.$\times$3 in. (about 23 cm$\times$7.5 cm) bottom sheet of hydrophobic, spinbonded nonwoven polyester having a measured weight of about 15 g/m$^2$. The bottom sheet is prefolded upwardly by means of heat and pressure which bonds the superposed sheets together. The resulting absorbent structure is useful as a sanitary napkin and has excellent properties of absorption and containment of menses exudate.

What is claimed is:

1. An absorbent structure comprising, by weight:
   (a) from about 1% to about 99% hydrogel selected from the group consisting of hydrolyzed acrylonitrile grafted starch, starch polyacrylates, cross-linked polyacrylates, and isobutylene maleic anhydride copolymers, or mixtures thereof;
   (b) from about 1% to about 99% of a fibrous cationic material which functions as an anion exchange material;
   (c) from 0% to about 99% of a fibrous anionic material which functions as a cation exchange material; and
   (d) from 0% to about 99% of a conventional absorbent material; said absorbent structure having an equilibrium pH of from about 5 to about 11 at the surface of said structure when said structure is saturated with synthetic urine.

2. An absorbent structure according to claim 1 which comprises a fibrous cation exchange material in an amount such that the ratio of exchange capacities of fibrous cation exchange material to fibrous anion exchange material is from about 10:1 to about 1:10.

3. An absorbent structure according to claim 1 comprising from about 1% to about 50% hydrogel.

4. An absorbent structure according to claim 3 having an equilibrium pH of from about 5.3 to about 9.

5. An absorbent structure according to claim 3 which comprises a homogeneous mixture of hydrogel, fibrous anion exchange material, and, optionally, fibrous cation exchange material.

6. An absorbent structure according to claim 1 comprising:
   (a) from about 1% to about 50% hydrogel;
   (b) from about 1% to about 70% of a fibrous anion exchange material;
   (c) from about 0% to about 50% of a fibrous cation exchange material; and
   (d) from about 0% to about 99% of a conventional absorbent material.

7. An absorbent structure according to claim 6 which comprises a fibrous cation exchange material in an amount such that the ratio of exchange capacities of fibrous cation exchange material to fibrous anion exchange material is from about 3:1 to about 1:10.

8. An absorbent structure according to claim 7 having an equilibrium pH of from about 5.3 to about 9.

9. An absorbent structure according to claim 6 which comprises a homogeneous mixture of hydrogel, fibrous anion exchange material, and, optionally, fibrous cation exchange material.

10. An absorbent structure according to claim 1 in which the fibrous anion exchange material is selected from the group consisting of diethyl amino ethyl cellulose, polyethyleneimine cellulose, amino ethyl cellulose, triethylaminoethyl cellulose, guanidoethyl cellulose, paraaminobenzyl cellulose, cellulose with triethanolamine coupled thereto through glyceryl and polyglyceryl chains, benzoylated diethyl amino ethyl cellulose, benzoylatednaphthoylated diethyl amino ethyl cellulose, and mixtures thereof.

11. An absorbent structure according to claim 1 which comprises a fibrous cation exchange material that is selected from the group consisting of cellulose phosphate, sulfoethyl cellulose, sulfonated chemothermal mechanical pulp, succinylated beet pulp, phosphorylated sugar beet pulp, citrus absorbent material, and mixtures thereof.

12. An absorbent structure according to claim 10 which comprises a fibrous cation exchange material that is selected from the group consisting of cellulose phosphate, sulfoethyl cellulose, sulfonated chemothermal mechanical pulp, succinylated sugar beet pulp, phosphorylated sugar beet pulp, citrus absorbent material, and mixtures thereof.

13. An absorbent structure according to claim 1 comprising:
   (a) from about 1% to about 50% hydrogel;
   (b) from about 1% to about 70% of a fibrous anion exchange material selected from diethylamino ethyl cellulose, polyethyleneimine cellulose, or mixtures thereof;
   (c) up to about 50% of a fibrous cation exchange material selected from cellulose phosphate, sulfonated chemothermal mechanical pulp, or mixtures thereof; and
   (d) from about 0% to about 50% of a conventional absorbent material; said absorbent structure having an equilibrium pH of from about 5.3 to about 7.0, and a ratio of exchange capcities of fibrous cation exchange material to fibrous anion exchange material from about 2:1 to about 1:3.

14. An absorbent structure according to claim 1 wherein said hydrogel is selected from the group consisting of starch polyacrylates and cross-linked polyacrylates.

15. A disposable absorbent product comprising:
   (a) a hydrophobic top sheet;
   (b) a liquid impervious backing sheet; and
   (c) an absorbent core comprising an absorbent structure according to claim 1, said core being placed between the backing sheet and the top sheet.

16. A disposable absorbent product comprising:
   (a) a hydrophobic top sheet;

(b) a liquid impervious backing sheet; and
(c) an absorbent core comprising an absorbent structure according to claim 4, said core being placed between the backing sheet and the top sheet.

17. A disposable absorbent product comprising:
(a) a hydrophobic top sheet;
(b) a liquid impervious backing sheet; and
(c) an absorbent core comprising an absorbent structure according to claim 6, said core being placed between the backing sheet and the top sheet.

18. A disposable absorbent product comprising:
(a) a hydrophobic top sheet;
(b) a liquid impervious backing sheet; and
(c) an absorbent core comprising an absorbent structure according to claim 10, said core being placed between the backing sheet and the top sheet.

19. A disposable absorbent product comprising:
(a) a hydrophobic top sheet;
(b) a liquid impervious backing sheet; and
(c) an absorbent core comprising an absorbent structure according to claim 11, said core being placed between the backing sheet and the top sheet.

20. A disposable absorbent product comprising:
(a) a hydrophobic top sheet;
(b) a liquid impervious backing sheet; and
(c) an absorbent core comprising an absorbent structure according to claim 12, said core being placed between the backing sheet and the top sheet.

21. A disposable absorbent product comprising:
(a) a hydrophobic top sheet;
(b) a liquid impervious backing sheet; and
(c) an absorbent core comprising an absorbent structure according to claim 13, said core being placed between the backing sheet and the top sheet.

* * * * *